US008535060B2

(12) United States Patent
Bianchi-Demicheli et al.

(10) Patent No.: US 8,535,060 B2
(45) Date of Patent: Sep. 17, 2013

(54) SYSTEM AND METHOD FOR DETECTING A SPECIFIC COGNITIVE-EMOTIONAL STATE IN A SUBJECT

(75) Inventors: Francesco Bianchi-Demicheli, Vessy/GE (CH); Stéphanie Ortigue, La Motte Servolex (FR)

(73) Assignee: Brain & Science LLC, Carson City, NV (US)

( * ) Notice: Subject to any disclaimer, the term of this patent is extended or adjusted under 35 U.S.C. 154(b) by 1391 days.

(21) Appl. No.: 11/845,179

(22) Filed: Aug. 27, 2007

(65) Prior Publication Data
US 2011/0027764 A1     Feb. 3, 2011

Related U.S. Application Data

(60) Provisional application No. 60/823,531, filed on Aug. 25, 2006.

(51) Int. Cl.
*G09B 23/28* (2006.01)

(52) U.S. Cl.
CPC .................................. *G09B 23/28* (2013.01)
USPC ...................................................... 434/236

(58) Field of Classification Search
USPC ....................................................... 434/236
See application file for complete search history.

(56) References Cited

U.S. PATENT DOCUMENTS

| | | | |
|---|---|---|---|
| 3,060,795 A | | 10/1962 | Corrigan et al. |
| 5,746,205 A | * | 5/1998 | Virsu et al. ................... 600/544 |
| 5,911,581 A | | 6/1999 | Reynolds et al. |
| 6,293,904 B1 | * | 9/2001 | Blazey et al. .................. 600/26 |
| 2003/0236451 A1 | | 12/2003 | El-Nokaly et al. |

FOREIGN PATENT DOCUMENTS

EP           0 995 458           2/2001

OTHER PUBLICATIONS

Paul J. Whalen et al, Masked Presentations of Emotional Facial Expressions Modulate Amygdala Activity without Explicit Knowledge, The Journal of Neuroscience, Jan. 1, 1998, 18(1):411-418.

* cited by examiner

*Primary Examiner* — Kesha Frisby
(74) *Attorney, Agent, or Firm* — Da Vinci Partners LLC; John Moetteli

(57) ABSTRACT

A system and method is disclosed which detects a specific cognitive-emotional mental state (e.g., passion) in a subject. The system and method utilizes different Internal Personalized Explorer (IPE) stimuli subliminally exposed to the subject on a visual display. Following exposure, the subject performs a target-specific cognitive task and a related behavior (e.g., deciding whether a briefly displayed string of letters is a word or not, and pressing a button to indicate the decision). The decision reaction lime for the behavior is recorded in a computer database. The reaction times are interpreted quantitatively to detect the relative intensity of the specific cognitive-emotional mental state in the subject. A reaction time for a specific individual IPE that is shorter than the mean reaction time for an IPE that does not evoke the emotional state indicates that the specific individual IPE did evoke the emotional state in the subject.

21 Claims, 3 Drawing Sheets

SYSTEM AND METHOD FOR DETECTING A SPECIFIC COGNITIVE-EMOTIONAL STATE IN A SUBJECT

PRIORITY CLAIM

This application claims the benefit of prior filed U.S. provisional application Ser. No. 60/823,531, filed Aug. 25, 2006, the content of which is incorporated herein by reference.

PATENT APPLICATION OWNER OF THE ENTIRE INTEREST

Hopitaux Universtaires de Geneve
24 rue Micheli-du-Crest
1211 Geneve 14 Switzerland

FIELD OF THE INVENTION

The present invention is in the field of behavioral diagnostic tools. Specifically, the present invention relates to detecting a specific emotional state in a subject. More specifically the present invention relates to the detection of subjective stimuli that evoke the specific emotion (e.g., passion), and the use of the stimuli to improve behavioral performance of a cognitive task.

BACKGROUND OF THE INVENTION

Intense inner cognitive-emotional states, such as love, passion, and goal-directed motivation, have been the source for some of the greatest achievements of mankind throughout the ages. The recent neuroscientific localization of passion within subcortico-cortical reward, motivation, cognitive and emotion systems in the human brain supports the hypothesis that passion is a goal-directed drive with predictable facilitation effects on cognitive behavior, rather than a pure and simple emotion.

Many scales, questionnaires or tests aim at evaluating a passionate mental state in a conscious way, but none of the existing tools does so in an objective manner. In the existing methods, the test subject is typically asked or induced to express verbally what his mental state is. The test subject's behaviors or responses to questions are unavoidably influenced by multiple external and internal factors, often obscuring the subject's true inner mental state, or preventing the subject from expressing it.

What is needed is a method and system of providing a cognitive, non-invasive, objective, and fast test, which allows determining quantitatively the inner cognitive-emotional state of participants on a sound neuroscientific basis. Also what is needed is a behavioral diagnostic tool that avoids the subjectivity inherent in the existing methods for evaluating cognitive-emotional states.

SUMMARY OF THE INVENTION

This invention relates to a behavioral method and system that detects specific cognitive-emotional states, such as passion, preference, and other mental states involving the subcortico-cortical reward, motivation, cognitive and emotion systems in the human brain. An essential feature of the invention is the subliminal Internal Personalized Explorer (IPE) injector which presents to the test subjects an Internal Personalized Explorer, a unique type of subliminal stimulus. It is believed that the present invention is the first practical application of the IPE technology platform. Further, the present invention is an un-blinded behavioral method and system for detecting a specific cognitive-emotional mental state in a subject.

The method and system of the present invention is based on neuroscientific evidence that demonstrates that shorter reaction times on a cognitive task that follows a particular subliminal stimulus are a reliable indicator of stronger intensity in the subject's mind of a passionate mental state with regard to that subliminal stimulus, in comparison to the intensity of passion/preference toward another subliminal stimulus. It does so by relying on correlations between the inner mental state being detected, and a measurable behavior that is cognitively unrelated to that mental state.

From the subject's perspective, the method and system is experienced as a computer-based test. Based on the results of the test, the method and system objectively detects the contemporaneous existence of a specific cognitive-emotional mental state in the mind of the subject. For purposes of this disclosure, the term cognitive-emotional state, or cognitive-emotional mental state, means any mental state that involves both cognitive and emotional centers, regions, systems, or functions of the human brain. Examples of cognitive-emotional states include love, hate, jealousy, preference, passion, goal-directed motivation, and even indifference.

The method and system detects the cognitive-emotional state objectively, in that the method and system relies on objective measurements of a cognitive behavior, and does not rely on any subjective information or analysis. The method and system detects the contemporaneous existence of a specific mental state, meaning that it detects a mental state that is existing in the subject's mind during the time when the test is conducted. The test is brief, typically lasting approximately 10 minutes. The test is non-invasive, meaning that no apparatus is connected or attached to the subject's body.

An essential feature of the method and system is that the subject is iteratively required to perform a meaningful target-specific cognitive task after being exposed to a subliminal stimulus. The subliminal stimulus used in the method and system is called an Internal Personalized Explorer, or IPE.

The IPE stimulus is typically a word or an image appearing on a visual display, but is not limited to these types of sensory input. The IPE stimulus is designed to match with the specific cognitive-emotional state sought to be detected in a subject. By matching, it is meant that there is a correspondence between the content or meaning of a particular IPE and the specific cognitive-emotional state that is the focus of the test.

The subliminal IPE stimulus differs from the standard subliminal stimulus that is commonly known in commercial advertising. In the present invention, the subliminal presentation of the IPE stimulus is not used to create an association with the target stimuli. It is not intended to be used with the aim to advertise any product or to influence consumer behavior, but can be used to assess behavior. The aim of the subliminal IPE presentation is to detect and explore an existing internal mental state, if it is present at the time in the subject.

The method and system is un-blinded, meaning that informing the subject prior to the test that subliminal stimuli will be used, and informing the subject that the purpose of the test is to detect a specific cognitive-emotional state, has no impact on the results obtained by the method and system. The method and system determines whether a specific cognitive-emotional state is present or not, regardless of whether the subject is informed about the use of subliminal stimuli prior to being tested.

The method and system is behavioral, meaning that what is measured is a behavior which the subject performs. The method and system requires the subject to perform a behavior.

In a preferred embodiment, the behavior was pressing a key on a keyboard of a computer, in response to a target-specific cognitive decision task-deciding whether a string of letters shown on a visual display (the target stimuli) is a word or not. What was measured was the reaction time of the behavior, meaning the elapsed time between presenting the target stimulus to the subject, and the subjects execution of the behavior indicating the subjects decision.

In the context of this disclosure, the target is the subject matter of the cognitive decision task that the subject is required to perform. The target is also referred to as the target stimulus. Each decision about an individual target is independent. The content or meaning of the target may or may not have a conceptual association with the IPE that precedes it in the course of the test. It is important that the task that the subject has to perform related to the target is cognitively relevant and "meaningful" for the participant subject. This helps to ensure that the subject is motivated and will make an effort to complete the required decision task as quickly as possible throughout the test.

Conducting the test involves repeating a cycle of successive steps, each cycle including exposing the subject to a subliminal IPE stimulus, followed by a mask or masking period to ensure the subliminal nature of the IPE stimulus. The subject is then required to perform the cognitive task. The subject's reaction time is recorded, i.e., the elapsed time between the onset of the target stimulus presentation and the completion of the behavior indicating the subject's decision on the cognitive task. For each of the two or more IPEs used as stimuli in the test, the mean reaction time is calculated for the subject's responses that followed exposure to that IPE. Then the mean reaction times for the individual IPEs are compared to each other.

Experiments using the method and system have demonstrated that shorter reaction times on the cognitive task reliably indicate stronger intensity in the subject's mind of a cognitive-emotional state that matches with the subliminal IPE stimulus given prior to the cognitive task target. See Addenda A and B.

Because the test in which the subject participates involves no self-reporting by the subject about any mental state, and relies instead on measuring a behavior that is not associated with the emotional content, if any, of the subliminal stimulus, the method and system avoids subjective artifacts in measured results.

An object of the invention is to provide a cognitive, non-invasive, objective, and fast test, which allows determining quantitatively the inner cognitive-emotional state of participants on a sound neuroscientific basis.

Another object of the invention is to provide a method and system that associates participants' answers (e.g., movement times, reaction times, accuracy) with subliminal stimulus presentations in the context of the study of the internal mental state of participants. This internal mental state can be emotional (e.g., love, hate, jealousy, preference, passion, etc.), and can also be neutral in comparison with an intense cognitive-emotional internal mental state.

Another object of the invention is to enable the objective evaluation of the internal mental state of participants, for it demonstrates at the unconscious level if the subject is in a specific internal mental state or not.

Another object of the invention is to provide a method and system in which the subjects cannot choose or guide their responses during the test. In a feature of the present invention, the subjects are either in a specific internal mental state for something/someone or they are not. The presence of the specific internal mental state is demonstrated by objective measurement of a cognitive behavior unrelated to the specific mental state being detected. In other words, the method and system reads the mind/emotion of the subject with respect to something or someone.

DETAILED DESCRIPTION OF THE PREFERRED EMBODIMENT(S)

Figure 1:
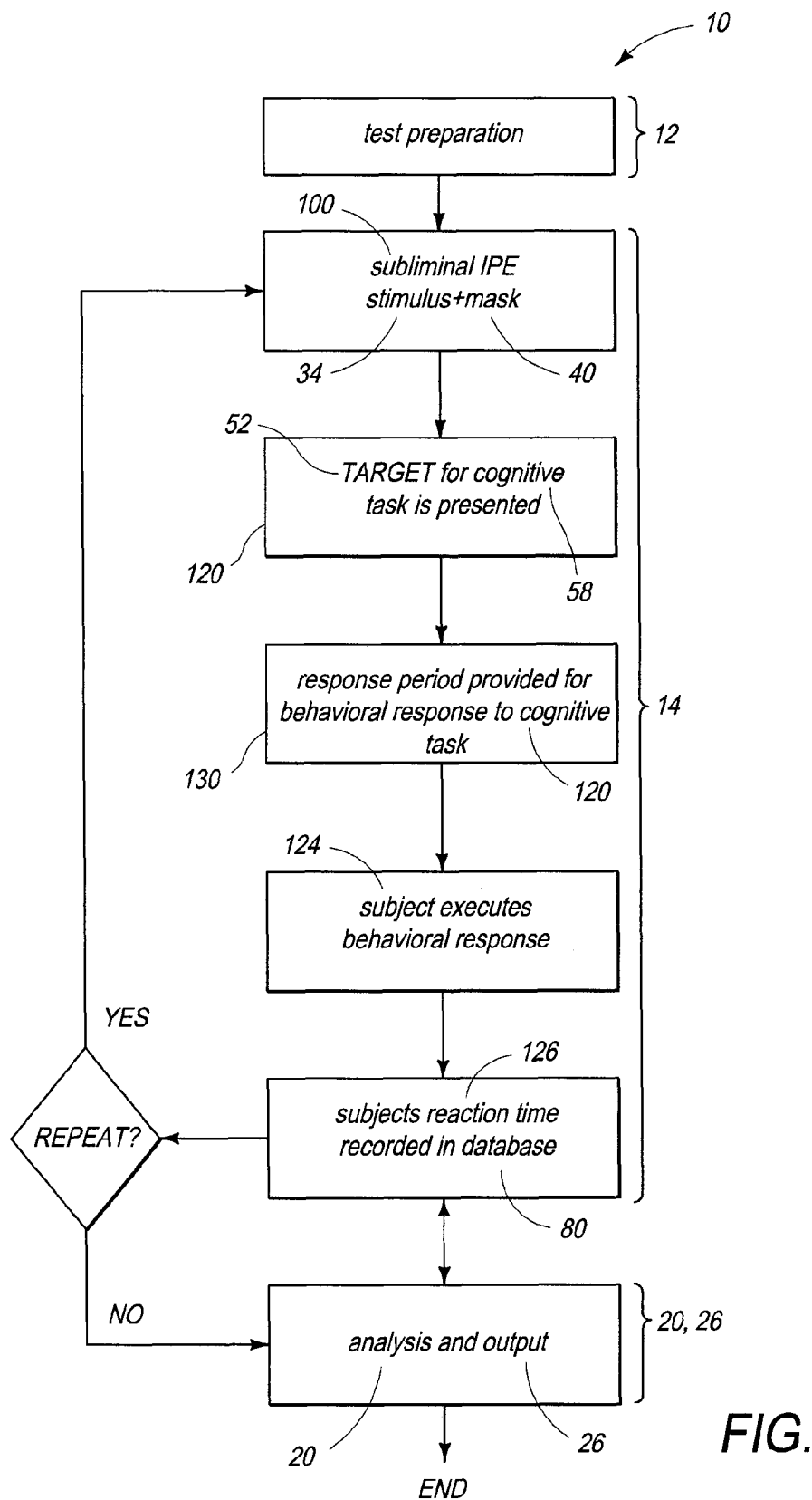
FIG. 1 illustrates the sequence of steps in the test administered to a subject, on a time scale.

The present invention is a behavioral method 10 that that operates on a computer system 44 and detects a specific cognitive-emotional state in a subject. Accordingly, this behavioral method 10 allows testing a subject for the presence and intensity of a preference or passion for a person, an activity, a product, or other entity in comparison to the subject's preference or passion for another entity of the same nature. For purposes of this disclosure, the subject is sometimes referred to as the participant in the test. As shown in FIG. 1, the behavioral method 10 involves test preparation 12 conducting test 14 on the subject and, using the system 44, analyzing test data 20 and outputting test results 26.

As part of the test preparation 12 prior to conducting the test 14, the administrator of the test defines the question that will be answered by the test results. Additionally, the test administrator selects at least two different Internal Personalized Explorer (IPE) stimuli 34 to be used in the test, which are the subliminal IPE stimuli 34 that will be used in the test 14. For example, the question can be whether the subject has an emotional preference for one of two consumer products, and the corresponding IPE stimuli 34 can be images or names of the two products. In another example, the question can be: what is the subject's favorite recreational activity at this time, and the corresponding IPE stimuli 34 can be the names of two or more different activities. In another example, the question can be: does the subject have an intense romantic love for a particular person, and the IPE stimuli 34 can be the name of that person, and the name of a neutral acquaintance of the subject. In another example, an additional IPE stimulus 34 can be a given name or word that has no particular significance to the subject. An IPE stimulus 34 is preferably presented to the subject via a visual display 46 of the computer system 44. The IPE stimulus 34 is presented on the visual display 46 as a subliminal display, i.e., the individual IPE stimulus 34 is presented on the visual display 46 for a time duration that is below the threshold of conscious perception of the stimulus and above the time duration for unconscious perception of the stimulus by the subject.

Once the IPE stimuli 34 to be used in the test 14 are defined, the mask(s) 40 to be used in the test 14 are defined. The purpose of the mask 40 is to ensure the subliminal character of the presentation of the IPE stimulus 34 and the subject's retention of the subliminal memory of the IPE stimulus 34. To accomplish this purpose, it is important that the mask be as meaningless a memory event stimulus to the subject as possible to avoid competition with and to enhance retention of the subliminal IPE stimulus memory. The mask 40 is presented in the masking step 110 for a brief, non-subliminal time duration of about 125 msec to 200 msec. In the preferred embodiment, the non-subliminal time duration was about 150 msec. The mask 40 is designed to fill the field of the visual display 46 and cover the field that was occupied, immediately prior to the mask by the IPE stimulus 34. For example, in the case where the IPE stimulus 34 is a word or a string of letters, the mask 40 can be a string of text characters that is not a word, or the mask can be a series of the "#" character, also referred to in this disclosure as the pound sign. In a preferred embodiment, the mask 40 is shown on the screen of the visual display 46 by text characters that are a size and a font similar to that of the preceding IPE stimulus.

Figure 2:
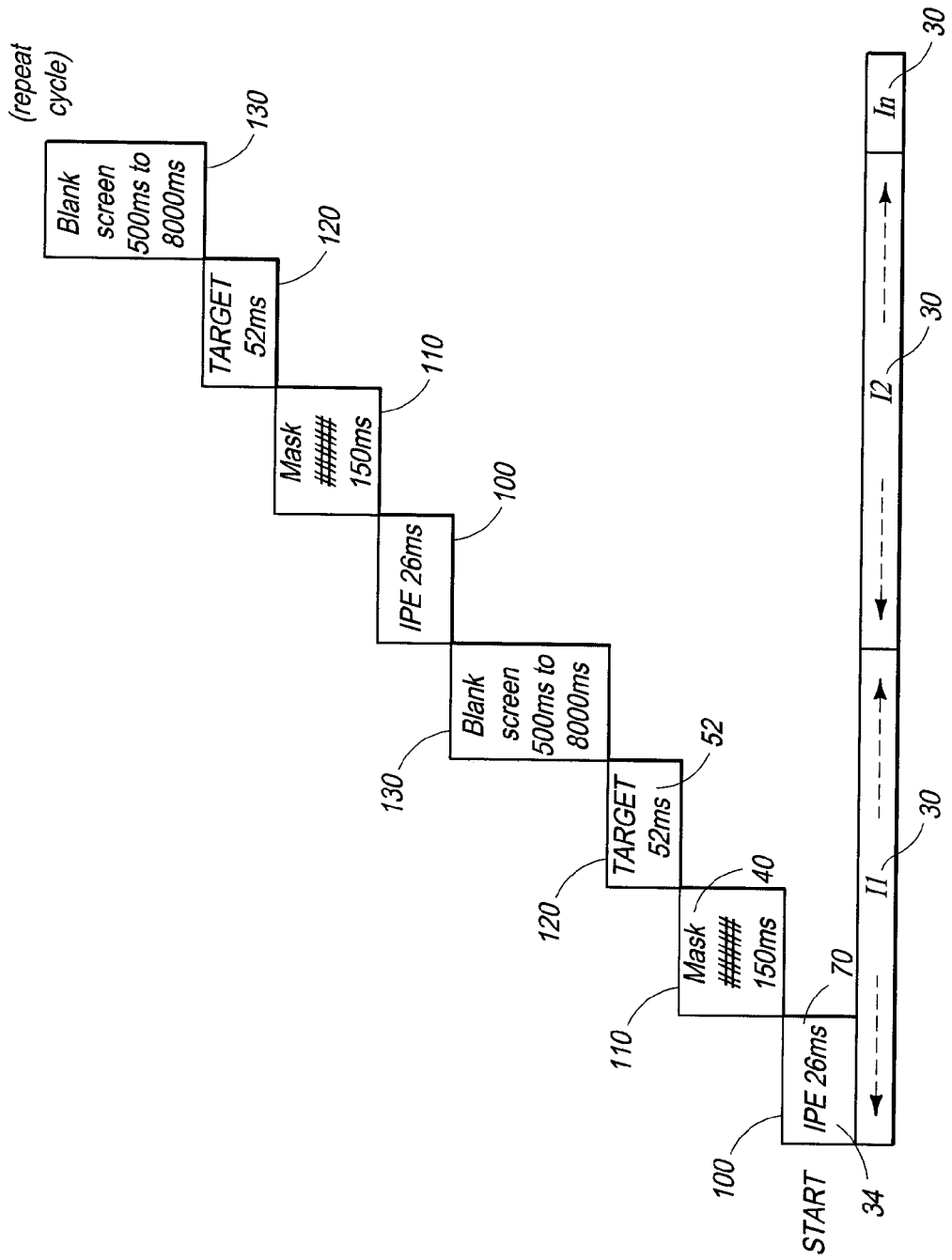
FIG. 2 is a flow chart showing the cycle of events that is iterated when using the method.
Figure 3:
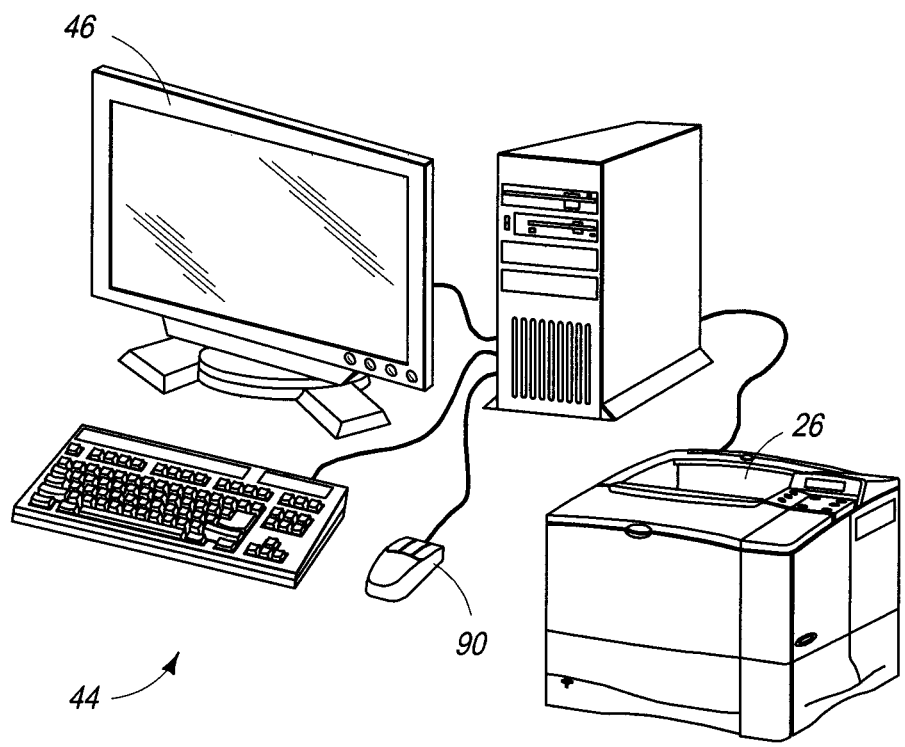
FIG. 3 is a schematic representation of the computer system useful for practice of the present invention.

In addition to the IPE stimuli 34 and the mask 40, also as part of preparing the test 14, the targets 52 to be presented during the test 14 as the subject matter of the cognitive task 58 are prepared. In one embodiment, the targets 52 were strings of letters, and the cognitive task 58 was to decide whether the target 52 is a word or is not a word. In other embodiments of the invention, the target stimuli may be images, video clips, smells, sounds, or any other type of stimulus that acts on the cognitive regions of the human brain. The IPE stimuli 34, the masks 40, and the targets 52 to be employed in the test 14 are embedded in the computer code that is used to administer the test 14 to the subject. FIG. 2 illustrates the administration of the test in an example timeline. The IPEs can be selected from the classes of IPEs 34 for the subject, which consist of: favored IPEs, neutral IPEs and indifferent IPEs.

The test 14 consists of a series of iterations or cycles 30 wherein in each cycle an IPE is subliminally presented and a cognitive recognition and behavioral task is performed. The test 14 itself comprises the step 100 of exposing the subject to a visual display 46 of an individual IPE stimulus 34 for a subliminal time duration 70. The exposing step 100 can comprise the exposing of the individual IPE stimulus 34 on the visual display 46 for a time duration that is about 20 msec to 30 msec. In the preferred embodiment illustrated, the exposing of the individual IPE stimulus 34 on the visual display 46 was for a duration of about 26 msec.

In the preferred embodiment illustrated, the visual display 46 is the video output device of a computer system 44. Immediately following the exposing step 100, a masking step 110 of the visual display 46 is performed. The visual display 46 presents the mask for a brief non-subliminal time duration. Following the masking step 110, the subject is presented with a meaningful target-specific visual cognitive recognition task 120. In the preferred embodiment, the cognitive task was a visual discrimination task 120 involving the target stimulus 52 presented on the visual display 46. Specifically, the cognitive task 120 presented on the visual display 46 was deciding whether a string of letters displayed for a short time was a word or not.

After the presentation 120 of the visual cognitive recognition task, the visual display 46 is blanked in a blanking step 130 for a randomly varied response period having at least a response period duration sufficient to complete the behavior 124 required of the visual cognitive recognition task 120. The related behavior 124 was to press a button to indicate the decision of the subject resulting from the cognitive task 120. In the preferred embodiment, the related behavior was the subject using an index finger to press a first button to indicate a "YES" decision and a second button to indicate a "NO" decision. While the cognitive task 120 and the related behavior were being performed, the visual display 46 presented a blank or a solid colored screen 132 to the subject for a randomly varied response period 134. The randomly varied response period 134 has a response period duration between about 0.5 sec and 8 sec.

A record is made in the database 80 of the subject's reaction time 126 to complete the behavior 124. The reaction time 126 is recorded via an input device 90 of the computer system 44 in a database 80 on the computer system 44. These steps constitute one iteration or cycle 30 of the test 14. Cycles 30 are repeated beginning with the exposing step 100 a sufficient number of times with different individual IPE stimuli 34 to generate a database 80 sufficient to determine a mean reaction time of the subject relative to each of the individual IPE stimuli 34 used and to create a data set of reaction times relative to specific IPE 34 and target 52 stimuli. An analytical/interpretive process 20 runs on the computer system 44 interprets the reaction time data of the data set, to detect the relative intensity of the specific cognitive-emotional mental state in the subject relative to the individual IPEs. The interpretive process 20 produces a result that reflects the specific cognitive-emotional state sought to be detected in the subject, and produces an output of the result in a written or a graphical form.

In another embodiment, using the computer system 44, the subliminal IPE image injector may inject subliminal images on a computer screen, for the primary purpose of enhancing the performance of the worker operating the computer. In such an embodiment, in an initialization step, images which invoke passion on the part of a particular user, determined through a questionnaire or by providing an input which enables the user to upload user-selected images that invoke passion within him, are stored. In an IPE injection step, these images are displayed to the user on a computer screen for an appropriate duration (e.g., 26 msec) and cycling according to empirical studies show improve a typical user's performance.

In an advantage, a method and system of cognitive, non-invasive, objective, and fast testing is provided, which allows determining quantitatively the inner cognitive-emotional state of participants on a sound neuroscientific basis.

In another advantage, a behavioral diagnostic tool is provided that avoids the subjectivity inherent in the existing methods for evaluating cognitive-emotional states.

In another advantage, the method and system avoids subjective artifacts in measured results.

In another advantage, the method and system provides a cognitive, non-invasive, objective, and fast test, which allows determining quantitatively the inner cognitive-emotional state of participants on a sound neuroscientific basis.

In another advantage, the method and system associates participants' answers (e.g., movement times, reaction times, accuracy) with subliminal stimulus presentations in the context of the study of the internal mental state of participants.

In another advantage, the method and system enables the objective evaluation of the internal mental state of participants, for it demonstrates at the unconscious level if the subject is in a specific internal mental state or not.

In another advantage, a method and system is provided in which the subjects cannot choose or guide their responses during the test.

Multiple variations and modifications are possible in the embodiments of the invention described here. Although certain illustrative embodiments of the invention have been shown and described here, a wide range of modifications, changes, and substitutions is contemplated in the foregoing disclosure. While the above description and the attached addenda (which is herein incorporated by reference) contain many specifics, these should not be construed as limitations on the scope of the invention, but rather as exemplifications of one or another preferred embodiment thereof. In some instances, some features of the present invention may be employed without a corresponding use of the other features. Accordingly, it is appropriate that the foregoing description be construed broadly and understood as being given by way of illustration and example only, the spirit and scope of the invention being limited only by the claims which ultimately issue in this application.

What is claimed is:

1. An un-blinded behavioral method for detecting a specific cognitive-emotional mental state in a subject, the method comprising the steps of:
consciously providing at least two different conscious and subjective stimuli, selected from one or more of a group of conscious, subjective stimuli designed to match a particular cognitive-emotional state in a particular subject, at least one of the group of conscious subjective stimuli being a test stimulus for testing whether the subject associates the test stimulus with a subsequent target-specific cognitive task that incorporates non-conscious components designed to match the particular cognitive-emotional state sought to be detected, said group including also a neutral conscious stimulus for which the subject is neutrally acquainted and an indifferent conscious, subjective stimulus which represents no particular significance to the subject, such stimuli referred to hereinafter as Internal Personalized Explorer (IPE) stimuli;
exposing the subject to a visual display of an individual IPE stimulus on a visual display device for a subliminal time duration, the visual display device being an output device of a computer system;
masking the visual display with a mask for a brief non-subliminal time duration;
following the masking step with the subject performing a meaningful target-specific cognitive task and a related behavior, wherein such target includes a sensory stimulus that incorporates non-conscious components designed to match the particular cognitive emotional state sought to be detected;
presenting on the visual display a randomly varied response period having at least a response period duration sufficient to complete the behavior, and recording a reaction time, whether voluntary or involuntary, and the accuracy of the behavior via an input device of the computer system in a database on the computer system;
repeating the exposing step a sufficient number of times with different individual IPEs to generate a database sufficient to determine a mean reaction time of the subject relative to each of the individual IPEs; and
interpreting the reaction time and accuracy of data of the data set, to detect the relative intensity of the specific cognitive-emotional mental state in the subject relative to the individual IPEs.

2. The un-blinded behavioral method of claim 1, wherein the providing step further comprises the IPEs being selected from the classes of IPE consisting of: a favored IPE, a neutral IPE and an indifferent IPE.

3. The un-blinded behavioral method of claim 1, wherein the exposing step further comprises the exposing of the individual IPE stimulus on the visual display for a time duration that is below the threshold of conscious perception of the stimulus and above the time duration for unconscious perception of the stimulus by the subject.

4. The un-blinded behavioral method of claim 1, wherein the exposing step further comprises the exposing of the individual IPE stimulus on the visual display for a time duration that is about 20 msec to 30 msec.

5. The un-blinded behavioral method of claim 1, wherein the exposing step further comprises that the exposing of the individual IPE stimulus on the visual display is for a duration of about 26 msec.

6. The un-blinded behavioral method of claim 1, wherein the masking step further comprises the mask being a field of the visual display being filled with text characters.

7. The un-blinded behavioral method of claim 1, wherein the masking step further comprises the mask being a field of the visual display being filled with text characters that are the "#" character.

8. The un-blinded behavioral method of claim 1, wherein the masking step further comprises the mask being a field of the visual display being filled with text characters that are a size and a font similar to that of the preceding IPE stimulus.

9. The un-blinded behavioral method of claim 1, wherein the masking step further comprises the brief non-subliminal time duration being about 125 msec to 200 msec.

10. The un-blinded behavioral method of claim 1, wherein the masking step further comprises the brief non-subliminal time duration being about 150 msec.

11. The un-blinded behavioral method of claim 1, wherein the masking step further comprises the brief non-subliminal time duration being sufficiently long to reduce competing memory events from interfering with retention of the individual IPE.

12. The un-blinded behavioral method of claim 1, wherein the following step further comprises the cognitive task being a visual discrimination task presented on the visual display.

13. The un-blinded behavioral method of claim 12, wherein the cognitive task presented on the visual display is deciding whether a string of letters displayed for a short time is a word or not.

14. The un-blinded behavioral method of claim 1, wherein the following step further comprises the related behavior being pressing a button to indicate a decision of the subject resulting from the cognitive task.

15. The un-blinded behavioral method of claim 14, wherein the related behavior is the subject using an index finger to press a button to indicate a decision of the subject resulting from the cognitive task.

16. The un-blinded behavioral method of claim 14, wherein the related behavior is the subject pressing a first button to indicate a "YES" decision and a second button to indicate a "NO" decision.

17. The un-blinded behavioral method of claim 1, wherein the presenting step further comprises a blank/solid screen being presented on the visual display.

18. The un-blinded behavioral method of claim 1, wherein the presenting step further comprises the randomly varied response period having a response period duration between about 0.5 sec and 8 sec.

19. The un-blinded behavioral method of claim 1, wherein the interpreting step further comprises using an interpretive computer process stored on the computer system.

20. The un-blinded behavioral method of claim 19, wherein the interpretive process stored on the computer system produces a result that reflects the specific cognitive-emotional state sought to be detected in the subject, and produces an output of the result in a written or a graphical form.

21. A system for detecting a specific cognitive-emotional mental state in a subject, the system comprising:
(a) a computer having:
a visual display for displaying visual stimulus,
a processor encoded with instructions performing the steps of:
consciously providing at least two different conscious and subjective stimuli, selected from one or more of a group of conscious, subjective stimuli designed to match a particular cognitive-emotional state in a particular subject, at least one of the group of conscious subjective stimuli being a test stimulus for testing whether the subject associates the test stimulus with a subsequent target-specific cognitive task that incorporates non-conscious components designed to match the particular cognitive-emotional state sought to be detected, said group including also a neutral conscious stimulus for which the subject is neutrally acquainted and an indifferent conscious, subjective stimulus which represents no particular significance to the subject, such stimuli referred to hereinafter as Internal Personalized Explorer (IPE) stimuli;

exposing the subject to a visual display of an individual IPE stimulus on a visual display device for a subliminal time duration, the visual display device being an output device of a computer system;

masking the visual display with a mask for a brief non-subliminal time duration;

presenting a target including a sensory stimulus that incorporates non-conscious components designed to match the particular cognitive emotional state sought to be detected and awaiting the subject performing a meaningful target-specific cognitive task and a related behavior;

presenting on the visual display a randomly varied response period having at least a response period duration sufficient to complete the behavior, and recording a reaction time, whether voluntary or involuntary, and the accuracy of the behavior via an input device of the computer system in a database on the computer system;

repeating the exposing step a sufficient number of times with different individual IPEs to generate a database sufficient to determine a mean reaction time of the subject relative to each of the individual IPEs; and interpreting the reaction time and accuracy of data of the data set, to detect the relative intensity of the specific cognitive-emotional mental state in the subject relative to the individual IPEs, storage for storing the inputs, response time, and other test criteria according to the encoded instructions and an input device for inputting responses from a test subject in response to stimuli administered in accordance with the encoded instructions method; and (b) a subliminal IPE image injector which, using software operating on the computer, is adapted to inject an IPE in a test subject by displaying selected visual stimulus to a test subject in sequences and for durations in accordance with the encoded instructions and according to a particular test protocol, and for receiving and processing inputs of the test subject according to the encoded instructions.

* * * * *

UNITED STATES PATENT AND TRADEMARK OFFICE
CERTIFICATE OF CORRECTION

PATENT NO.     : 8,535,060 B2
APPLICATION NO. : 11/845179
DATED          : September 17, 2013
INVENTOR(S)    : Francesco Bianchi-Demicheli It is certified that error appears in the above-identified patent and that said Letters Patent is hereby corrected as shown below:

In the Specification

In Col. 1, line 11, delete the following (lines 11-16):

"PATENT APPLICATION OWNER OF THE
    ENTIRE INTEREST

Hopitaux Universitaires de Geneve
24 rue Micheli-du-Crest
1211 Geneve 14 Switzerland"

In Col. 4, line 18, replace the phrase "method 10 that that" with --method 10 that--

Signed and Sealed this
Twenty-sixth Day of November, 2013

Margaret A. Focarino
*Commissioner for Patents of the United States Patent and Trademark Office*